US011653830B2

(12) United States Patent
Gründig et al.

(10) Patent No.: US 11,653,830 B2
(45) Date of Patent: May 23, 2023

(54) MULTI-VIEW OPHTHALMIC DIAGNOSTIC SYSTEMS

(71) Applicant: NOVARTIS AG, Basel (CH)

(72) Inventors: Martin Gründig, Rangsdorf (DE); Peter Zieger, Teltow (DE)

(73) Assignee: Alcon Inc., Fribourg (CH)

( * ) Notice: Subject to any disclaimer, the term of this patent is extended or adjusted under 35 U.S.C. 154(b) by 640 days.

(21) Appl. No.: 16/213,602

(22) Filed: Dec. 7, 2018

(65) Prior Publication Data

US 2019/0191990 A1 Jun. 27, 2019

Related U.S. Application Data

(60) Provisional application No. 62/608,917, filed on Dec. 21, 2017.

(51) Int. Cl.
*A61B 3/10* (2006.01)
*A61B 3/103* (2006.01)
*A61B 3/00* (2006.01)
*A61B 3/107* (2006.01)

(52) U.S. Cl.
CPC ............ *A61B 3/102* (2013.01); *A61B 3/0008* (2013.01); *A61B 3/103* (2013.01); *A61B 3/107* (2013.01)

(58) Field of Classification Search
CPC ....... A61B 3/102; A61B 3/0008; A61B 3/103; A61B 3/107; A61B 3/1035; A61B 3/117; A61B 3/1173; A61B 3/1176; A61B 5/0033; A61B 5/0073; A61B 2090/3735
USPC .................................. 351/206, 211, 212, 246
See application file for complete search history.

(56) References Cited

U.S. PATENT DOCUMENTS

| | | | |
|---|---|---|---|
| 9,538,911 B2 | 1/2017 | Artsyukhovish et al. | |
| 2010/0097573 A1* | 4/2010 | Verdooner | A61B 3/14 351/206 |
| 2013/0107208 A1* | 5/2013 | Endo | A61B 3/14 351/206 |
| 2015/0272439 A1* | 10/2015 | Ng | A61B 3/14 351/206 |
| 2016/0106581 A1* | 4/2016 | Gonzalez | A61B 5/704 128/845 |
| 2016/0135679 A1* | 5/2016 | Frisken | G01B 9/02044 351/212 |
| 2016/0345820 A1* | 12/2016 | Frisken | A61B 3/1225 |

FOREIGN PATENT DOCUMENTS

| | | |
|---|---|---|
| WO | 2012130818 A1 | 10/2012 |
| WO | WO2014149839 A1 | 9/2014 |
| WO | 2014155286 A1 | 10/2014 |
| WO | 2015121756 A2 | 8/2015 |
| WO | WO2016187675 A1 | 12/2016 |

\* cited by examiner

*Primary Examiner* — Travis S Fissel

(57) ABSTRACT

A multi-view diagnostic system includes an OCT engine and a plurality of optical elements defining a plurality of beam paths between the OCT engine and an ophthalmic target, with each beam path corresponding to a different viewing angle of the ophthalmic target. The system also includes a scanner to direct OCT imaging beams generated by the OCT engine toward the ophthalmic target along each respective beam path. Instructions stored in memory are executable by a processor to determine a characteristic of the ophthalmic target based on OCT light reflected by the ophthalmic target along each respective beam path and detected by the OCT engine.

11 Claims, 5 Drawing Sheets

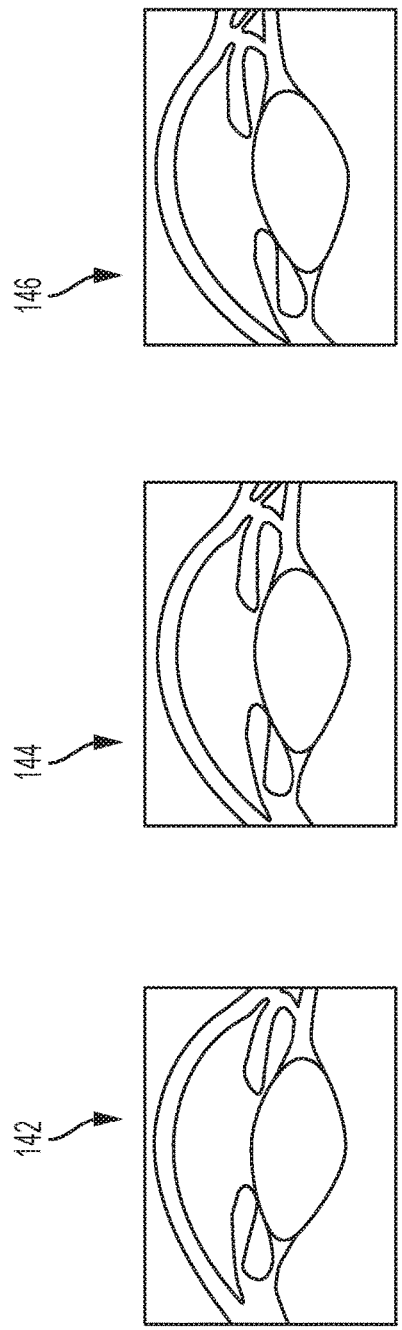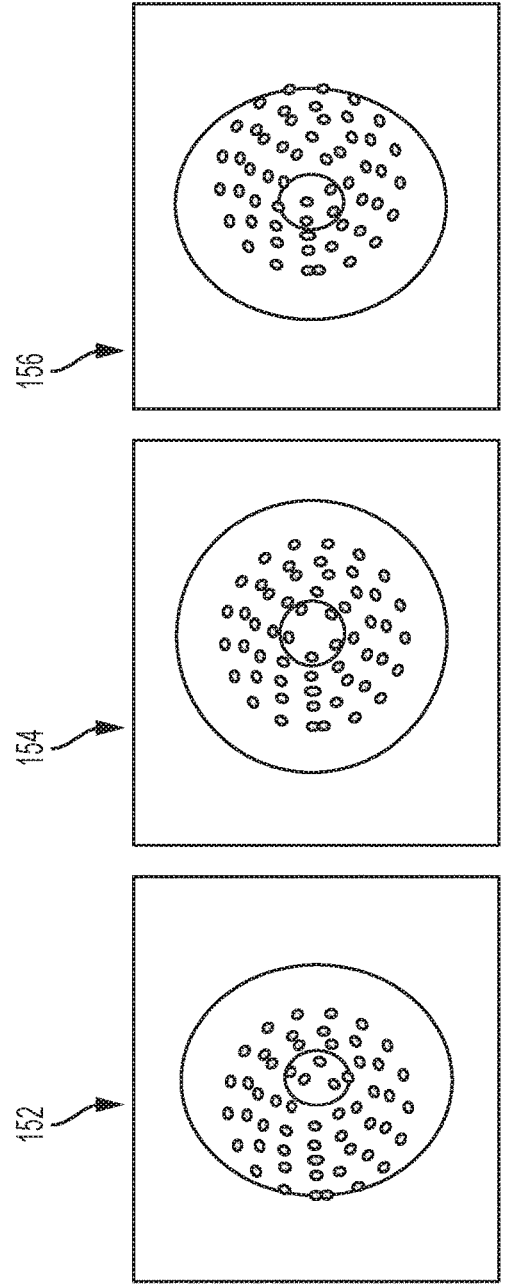
FIG. 1B
FIG. 1C

US 11,653,830 B2

MULTI-VIEW OPHTHALMIC DIAGNOSTIC SYSTEMS

PRIORITY CLAIM

This application claims the benefit of priority of U.S. Provisional Patent Application Ser. No. 62/608,917 titled "MULTI-VIEW OPHTHALMIC DIAGNOSTIC SYSTEMS," filed on Dec. 21, 2017, whose inventors are Martin Gruendig and Peter Zieger, which is hereby incorporated by reference in its entirety as though fully and completely set forth herein.

FIELD

The present disclosure relates to ophthalmic systems, and more particularly to multi-view ophthalmic diagnostic systems.

BACKGROUND

Optical Coherence Tomography (OCT) is an imaging technique widely adopted in the biomedical fields, including ophthalmology. OCT systems perform high-resolution, cross sectional imaging in semitransparent samples (such as biological tissues) by measuring the echo time delay of reflected light. OCT may be used in ophthalmic diagnostic systems to assist ophthalmic surgeons in preoperative diagnostics to support cataract and/or corneal refractive surgery, as well as with precision cutting and/or removal of tissues of an eye such as the vitreous humor.

SUMMARY

In certain embodiments, a multi-view diagnostic system includes an OCT engine and a plurality of optical elements defining a plurality of beam paths between the OCT engine and an ophthalmic target, with each beam path corresponding to a different viewing angle of the ophthalmic target. The system also includes a scanner configured to direct OCT imaging beams generated by the OCT engine toward the ophthalmic target along each respective beam path. The system further includes a processor and instructions stored in a memory. The instructions are executable by the processor to determine a characteristic of the ophthalmic target based on OCT light reflected by the ophthalmic target along each respective beam path and detected by the OCT engine.

In certain embodiments, a method includes directing multiple OCT imaging beams toward an ophthalmic target along respective beam paths, with each beam path being defined by a plurality of optical elements and corresponding to a different viewing angle of the ophthalmic target. The method further includes receiving, along each of the beam paths, reflected OCT light from the ophthalmic target, and determining one or more characteristics of the ophthalmic target based on the detected OCT light reflected by the ophthalmic target along each respective beam path.

In certain embodiments, multi-view diagnostic system includes a plurality of optical elements defining a plurality of beam paths between a beam splitter and an ophthalmic target, with each beam path corresponding to a different viewing angle of the ophthalmic target. The system also includes an OCT imaging system optically aligned with the beam splitter. The OCT imaging system is configured to direct OCT imaging beams toward the ophthalmic target along each respective beam path, and detect OCT light reflected by the ophthalmic target along each respective beam path. The system further includes a camera optically aligned with the beam splitter and configured to detect illumination light reflected by the ophthalmic target along each respective beam path. The system further includes a processor and instructions stored in a memory. The instructions are executable by the processor to determine a refractive index of at least one of a cornea, aqueous humor, a lens, or vitreous humor of the ophthalmic target based on the detected OCT light, and determine curvatures of the ophthalmic target based on the detected illumination light reflected by the ophthalmic target along each respective beam path.

Certain embodiments may provide one or more technical advantages, in some instances. For example, in some instances, more accurate curvature measurements of the central part of the cornea may be obtained. In addition, in some instances, an overall increased accuracy in measuring the corneal anterior and posterior shape may be obtained. Furthermore, in some instances, a determination of the in-vivo refractive indices of the cornea, the anterior chamber, or other portions of an ophthalmic target can be made. This information can be used to determine an actual form of an ophthalmic target, and can be used to obtain a more optimal intraocular lens (IOL) profile.

These and other advantages will be apparent to those skilled in the art in view of the present drawings and specification.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIGS. 1B and 1C illustrate perspective views of an ophthalmic target provided by the ophthalmic diagnostic system of FIG. 1A.

Figure 1A:
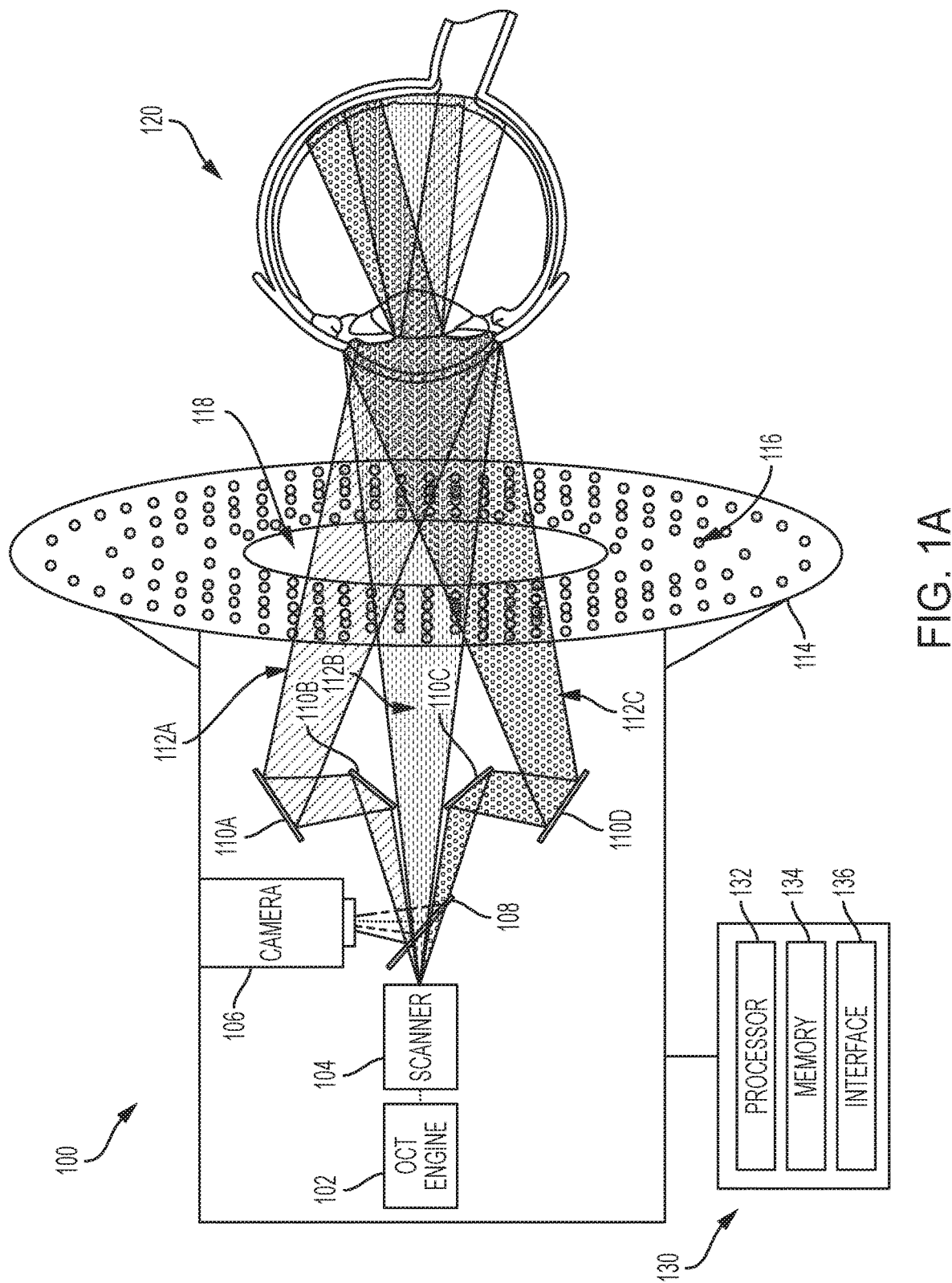
FIG. 1A illustrates a block diagram of an example multi-view ophthalmic diagnostic system.

One skilled in the art will understand that the drawings, described below, are for illustration purposes only, and are not intended to limit the scope of applicant's disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

FIG. 1A illustrates a block diagram of an example multi-view ophthalmic diagnostic system 100. The example system 100 includes an OCT engine 102, a scanner 104, camera 106, beam splitter 108, mirrors 110 that define multiple beam paths 112, and an illumination source 114 that includes multiple illumination point sources 116. As described herein, the ophthalmic diagnostic system 100 is configured to determined diagnostic information about an ophthalmic target, such as the ophthalmic target 120 shown in FIG. 1A, based on light (e.g., OCT light from the OCT engine, illumination light from the illumination point sources 116, or both) reflected along different beam paths 112. The ophthalmic target 120 may include one or more refractive tissues of the eye, such as, for example, the cornea, aqueous humor, lens, or vitreous humor.

The example OCT engine 102 includes components that are configured to generate OCT imaging beams and receive OCT light reflected by the ophthalmic target 120. The OCT engine 102 may include a pulsed laser source, an interferometer, a photodetector, and one or more other optical components (e.g., mirrors, beam splitters, etc.). In some instances, the OCT engine 102 may be a commercially-available OCT engine. The example scanner 104 includes a set of manipulatable mirrors that can receive the OCT imagine beams from the OCT engine 102 and direct the beams along one of the beam paths 112 within the system 100. The scanner 104 can be implemented as a microelectromechanical system (MEMS), a mirror galvanometer, or in another manner. The OCT engine 102 and the scanner 104 may be together referred to as an OCT imaging system. In some cases, the OCT engine 102 and scanner 104 are distinct apparatuses within the system 100 (e.g., as shown in FIG. 1A). In other cases, the OCT engine 102 and scanner 104 are contained within the same apparatus.

The example camera 106 is a high-resolution camera that is configured to receive illumination light emitted by the illumination point sources 116 and reflected by the ophthalmic target 120 back through the different beam paths 112. In some instances, the camera 106 may be a commercially-available camera.

In the example shown, there are three distinct beam paths 112A, 112B, 112C. As shown in FIG. 1A, the beam paths 112 may converge and intersect within the ophthalmic target 120. Other examples may include additional or fewer beam paths 112. Each beam path 112 may provide the OCT engine 102 or the camera 106 with a different perspective view of the ophthalmic target 120. As shown, the beam path 112B allows a straight-on view of the ophthalmic target 120 by the OCT engine 102 and the camera 106 (e.g., a view corresponding to an optical axis or a visual axis of the ophthalmic target 120). The beam paths 112A, 112C are defined by the optical elements 110 (i.e., beam path 112A is defined by optical elements 110A, 110B, and beam path 112C is defined by optical elements 110C, 110D) and provide side views of the ophthalmic target 120 as shown. In the example shown, the optical elements 110 are static mirrors. The optical elements 110 may include other types of optical elements. As described further below, multiple perspective views of the ophthalmic target 120 may allow for one or more characteristics of the ophthalmic target 120 to be measured in a more accurate manner.

The example beam splitter 108 is an optical element configured to pass a portion of incident light and reflect another portion of incident light, splitting the incident beam. For instance, in the example shown in FIG. 1A, the beam splitter 108 is configured to allow a portion of OCT or illumination light reflected from the ophthalmic target 120 to pass back toward the OCT engine 102 and another portion of the reflected light to reflect toward the camera 106. The beam splitter 108 may be formed by a film (e.g., a dielectric film) deposited on one or more surfaces of a transparent or translucent material (e.g., glass). For example, the beam splitter 108 may be implemented as a dielectric mirror, a metal-coated mirror, a beam splitter cube, or in another manner.

In the example shown, the illumination source 114 is coupled to the system 100. However, in other examples, the illumination source 114 may be distinct from the system 100. The illumination source 114 includes multiple illumination point sources 116. The illumination point sources 116 can be arranged in a circular manner around an aperture 118 that allows the OCT imaging beams or other light to pass through to or from the system 100. In the example shown, the illumination point sources are arranged in concentric circles. The illumination point sources 116 may be implemented as light emitting diodes (LEDs), organic LEDs (OLEDs), or another type of visible light source.

In the example shown, the ophthalmic diagnostic system 100 is coupled to a computer system 130 that includes a processor 132, memory 134, and an interface 136. The example processor 132 executes instructions, for example, to generate output data based on data inputs. The instructions can include programs, codes, scripts, or other types of data stored in memory. Additionally or alternatively, the instructions can be encoded as pre-programmed or re-programmable logic circuits, logic gates, or other types of hardware or firmware components. The processor 132 may be or include a general purpose microprocessor, as a specialized co-processor or another type of data processing apparatus. In some cases, the processor 132 may be configured to execute or interpret software, scripts, programs, functions, executables, or other instructions stored in the memory 134 to determine one or more characteristics of the ophthalmic target 120 based on data obtained by the OCT engine 102, the camera 106, or both. In some instances, the processor 132 includes multiple processors.

The example memory 134 includes one or more computer-readable media, for example, a volatile memory device, a non-volatile memory device, or both. The memory 134 can include one or more read-only memory devices, random-access memory devices, buffer memory devices, or a combination of these and other types of memory devices. The memory 134 may store instructions that are executable by the processor 132.

The example interface 136 provides communication between the pattern validation system 108 and one or more other devices. For example, the interface 136 may include one or more interfaces allowing interaction with the ophthalmic diagnostic system 100 by a user, such as a keyboard, mouse, touchscreen, and the like.

In certain embodiments, the computer system 130 obtains data from the OCT engine 102, the camera 106, or both and processes the data to determine one or more characteristics of the ophthalmic target 120. In some embodiments, the computer system 130 may use OCT techniques and first and second order Purkinje ray tracing techniques to measure simultaneously the curvature and anatomy of all refractive surfaces of the ophthalmic target 120 from the different perspective views provided. By using a multi-view system such as the one shown in FIG. 1A, more accurate curvature measurements of the central part of the cornea may be obtained, an overall increased accuracy in measuring the corneal anterior and posterior shape may be obtained, and a determination of the in-vivo refractive indices of the cornea and the anterior chamber may be made. For instance, with multiple views, a three-dimensional model of a sclera or other portion of the ophthalmic target 120 can be generated (as opposed to the two-dimensional model that is available with only one view). In addition, multiple views allow for measurements of a distance between the camera 106 and the ophthalmic target 120. In addition, with multiple views, reflections from the corneal apex can be detected (whereas a single view system cannot). Corneal apex reflections allow for a more complete understanding of ophthalmic target 120, and obtaining shape information (e.g., a curvature) for the corneal apex may be helpful in modeling the ophthalmic target 120.

In some instances, the computer system 130 may generate a three-dimensional eye model of the ophthalmic target based on the OCT data. The model be used in a ray-tracing analysis that determines an intraocular lens (IOL) profile. The IOL profile may include a power and position of the IOL within the ophthalmic target. The IOL profile may also include a shape, a media, or an astigmatism of an IOL.

Figure 3A:
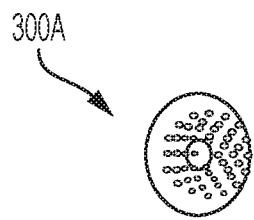
FIGS. 3A-3D illustrate example configurations of a multi-view ophthalmic diagnostic system.
Figure 3B:
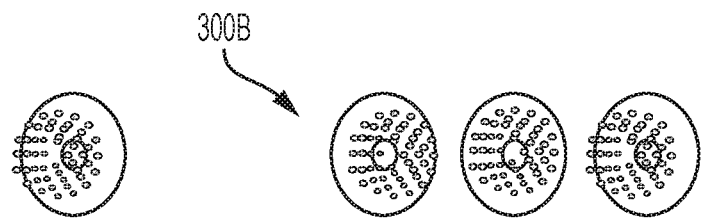
Figure 3C:
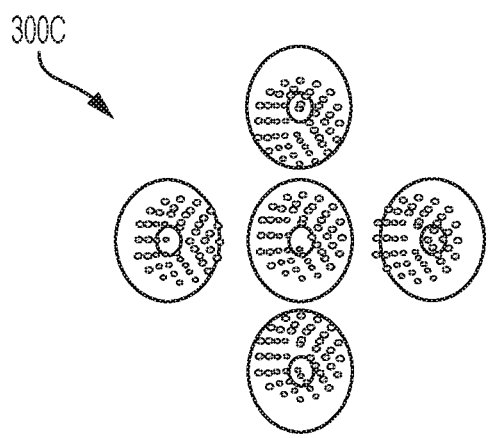

For example, by detecting first order Purkinje reflections of the illumination point sources 116 on the front side of the cornea, the computer system 130 can determine efficiently the anterior corneal curvature. In addition, by detecting second order Purkinje reflections on the backside of the cornea, the computer system 130 can determine measurements of the curvature of the posterior cornea. The OCT engine 102 may perform a three-dimensional elevation scan of the ophthalmic target 120. The combination of first and second order Purkinje ray tracing analysis and the OCT data gathered by the OCT engine give accurate information of the cornea as well as information about the depth of the ophthalmic target 120. By multiplying the views of the illumination light reflections, the overall curvature density is increased by a factor of N, where N is the number of perspective views offered by the system 100. For instance, if a triple view configuration is used (e.g., as shown in FIG. 1A), the curvature density is increased by a factor of three. Other multi-view configurations are shown in FIGS. 3A-3C and described further below.

The example system 100 may include additional, fewer, or different components from those shown in FIG. 1A, in certain embodiments. For example, the system 100 can include fewer (e.g., two) beam paths, or additional beam paths defined by additional mirrors (e.g., as shown in FIGS. 3B, 3C). As another example, the system 100 can include multiple cameras to achieve multiple views of the ophthalmic target, as opposed to using the beam paths 112 to achieve the multiple views for the camera 106.

FIGS. 1B and 1C are example perspective views of an ophthalmic target provided by the ophthalmic diagnostic system of FIG. 1A. The perspective views 142, 144, 146 provided by the OCT engine 102 are shown in FIG. 1B, and the perspective views 152, 154, 156 provided by the camera 106 are shown in FIG. 1C. In the examples shown, the views 142, 152 are associated with the beam path 112A, the views 144, 154 are associated with the beam path 112B, and the views 146, 156 are associated with the beam path 112C. In certain embodiments, the views 142, 144, 146 may be used to determine a refractive index of one or more of the tissues of the ophthalmic target 130. For example, the views 142, 144, 146 may be aligned with one another such that the respective surfaces of the target 120 match. Aligning the images may include generating a model with a parameterization of each of the tissues in the target 120, where the parameters include a refractive index for one or more of the tissues. A refractive index (or indices) may be determined by a best fit approach. For example, a least squares technique can be used to align the parameterized models and determine a refractive index for one or more of the tissues of the target 120. In some cases, the views 152, 154, 156 may be used in the parameterization of the target 120, and the parameterization of the camera view may be used in the determination of a refractive index for one or more of the tissues of the target 120 (e.g., the cornea, aqueous humor, a lens, or vitreous humor).

Figure 2B:
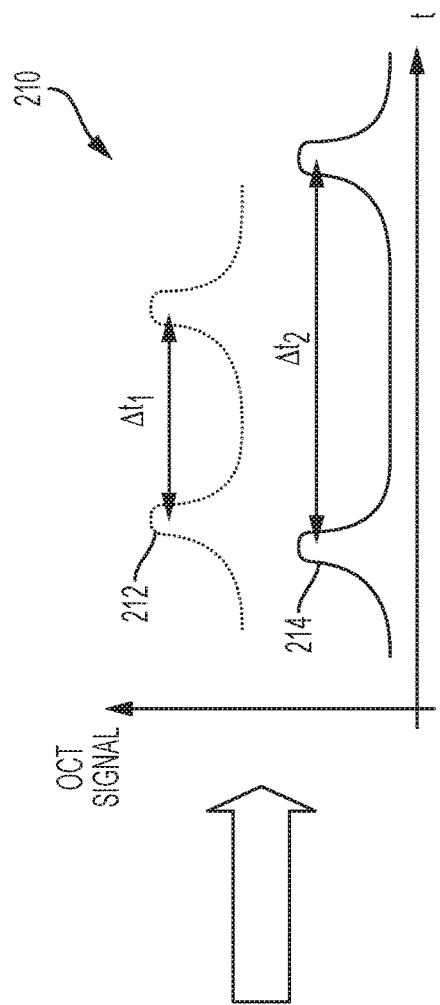
FIGS. 2A-2B illustrate optical delay difference in an OCT signal depending on different angle of incidents to be used for an example ray tracing process for determining a refractive index of an ophthalmic target using OCT imaging beams.
Figure 2A:
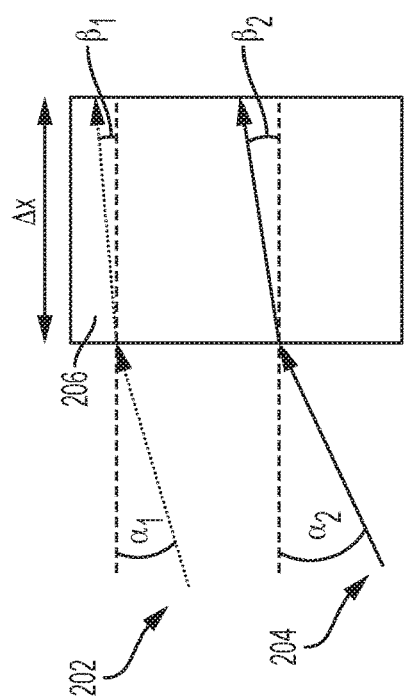

FIGS. 2A-2B are diagrams showing optical delay difference in OCT signal depending on different angle of incidents to be used for an example ray tracing process for determining a refractive index of an ophthalmic target using OCT imaging beams. In the example shown in FIG. 2A, optical beams 302 and 304 are transmitted toward a target material 306 at different incident angles $\alpha_1$ and $\alpha_2$, respectively, and accordingly traverse the target material 306 at different angles $\beta_1$ and $\beta_2$, respectively (based on Snell's law). The difference in the angles $\beta_1$ and $\beta_2$ causes the beams 302 and 304 to traverse the target material 306 of thickness $\Delta x$ over different distances, causing a difference in the amount of time each beam spends within the target material 306. In the example shown in FIG. 2B, an example OCT signal is shown for both beams 302, 304, where $\Delta t_{1,2}$ describe the arrival time difference of the OCT signal at the front and back side of the target material 306 for the respective beams 202, 204. If initial conditions are known (i.e., $\alpha_1$ and $\alpha_2$), the refractive index off the target material 306 can be computed.

Figure 3D:
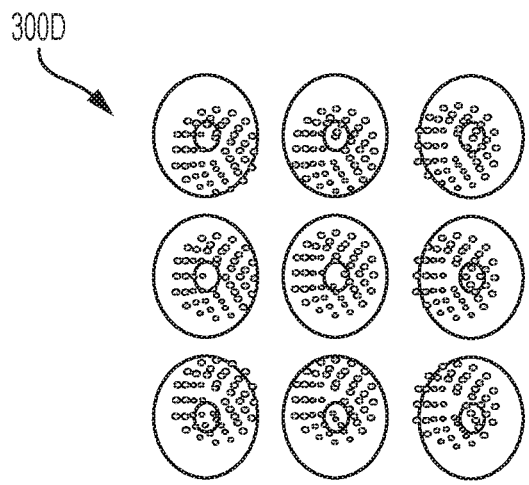

FIGS. 3A-3D are diagrams showing example configurations 300 of a multi-view ophthalmic diagnostic system. The example configuration 300A shown in FIG. 3A is a double view configuration, with two off-center perspective views of an ophthalmic target. The example configuration shown in FIG. 3B is a triple view configuration 300B similar to the system 100 of FIG. 1A, with three different perspective views of an ophthalmic target. The example configuration shown in FIG. 3C is a quintuple view configuration 300C with five different perspective views of the ophthalmic target, and the example configuration shown in FIG. 3D is a nonuple view configuration 300D with nine different perspective views of the ophthalmic target. In some cases, the nonuple view configuration 300D may be beneficial with squared sensors in the camera of the ophthalmic diagnostic system. Other multi-view configurations may also be implemented.

Figure 4:
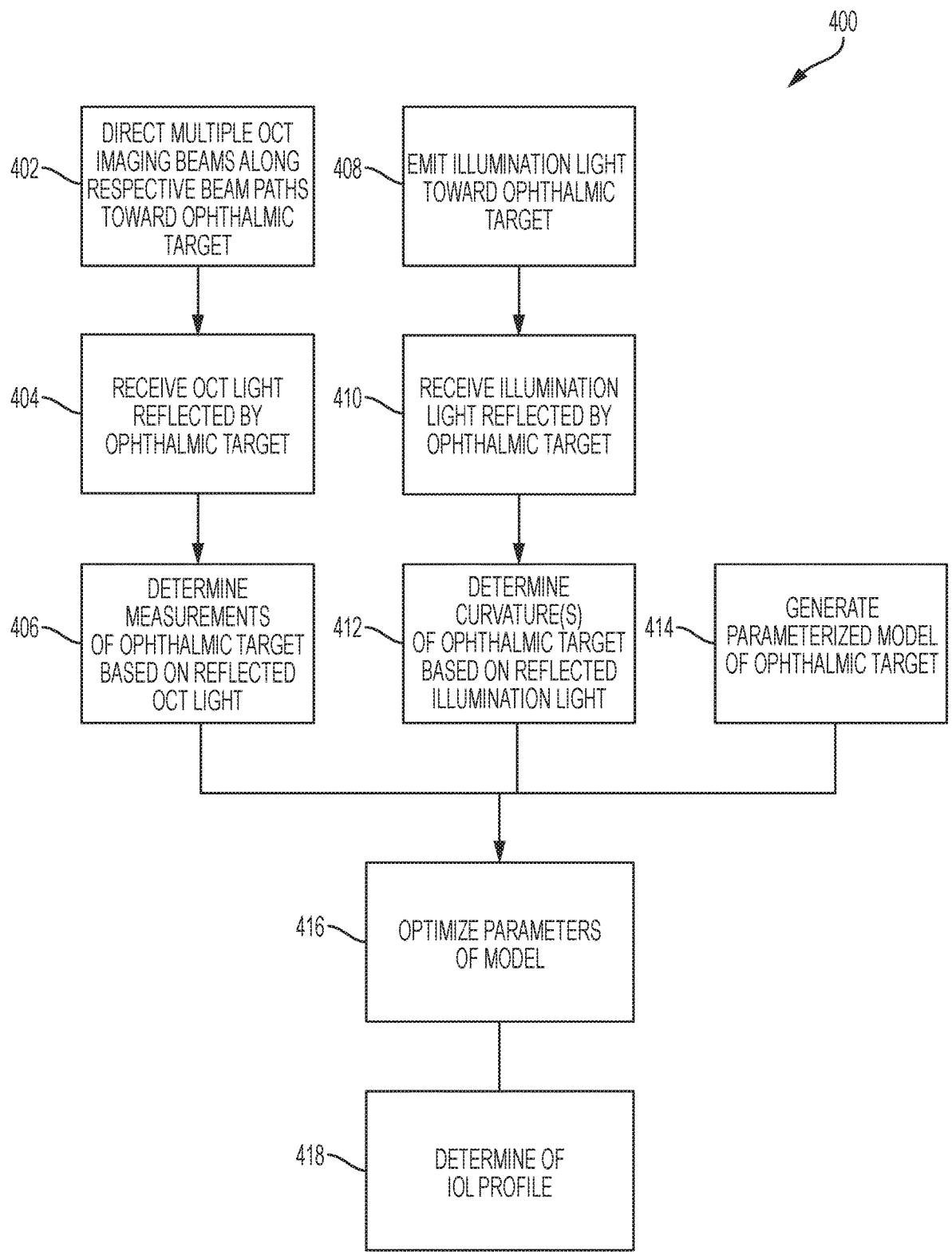
FIG. 4 illustrates example process of determining measurements corresponding to an ophthalmic target using a multi-view ophthalmic diagnostic system.

FIG. 4 is a flow diagram showing an example process of determining measurements corresponding to an ophthalmic target using a multi-view ophthalmic diagnostic system. Operations in the example process 400 may be performed by a data processing apparatus (e.g., the processor 132 of the example computer system 130 of FIG. 1A). The example process 400 may include additional or different operations, and the operations may be performed in the order shown or in another order. In some cases, one or more of the operations shown in FIG. 4 are implemented as processes that include multiple operations, sub-processes, or other types of routines. In some cases, operations can be combined, performed in another order, performed in parallel, iterated, or otherwise repeated or performed another manner.

At 402, multiple OCT imaging beams are directed along respective beam paths toward an ophthalmic target. The OCT imaging beams may be generated by an OCT imaging device, such as an OCT engine. For example, referring to FIG. 1A, the OCT imaging beams may be generated by the OCT engine 102 and directed along each of the beam paths 112. In some instances, the OCT imaging beams may perform an OCT scan along each of the respective beam paths. In some cases, the scans may be performed in a sequential manner. For example, referring again to FIG. 1A, the OCT imaging beams may perform a first OCT scan along the beam path 112A, a second OCT scan along the beam path 112B, and a third OCT scan along the beam path 112C. The OCT imaging beams may be directed along each respective path by a scanner that includes one or more manipulatable mirrors. For example, referring again to FIG. 1A, the scanner 104 may selectively direct OCT imaging beams generated by the OCT engine 102 along one of the beam paths 112A, 112B, 112C.

At 404, OCT light reflected by the ophthalmic target is received. The reflected OCT light may be received at the OCT imagine device (e.g., an OCT engine) that transmitted the initial OCT imaging beams. The OCT light may include the OCT imaging beams transmitted at 402 and reflected back by the ophthalmic target. The reflected OCT light may travel along the beam path through which the initial OCT imaging beam traveled. For example, referring to FIG. 1A, OCT imaging beams transmitted by the OCT engine 102 along the beam path 112A, may be reflected by the ophthalmic target 120 and travel back along the beam path 112A toward the beam splitter 108, which transmits a portion of the reflected OCT light toward the OCT engine 102, where it is received and detected.

At 406, measurements of the ophthalmic target are determined based on the received OCT light. The measurements may include a thickness of a tissue in the ophthalmic target (e.g., a cornea thickness or lens thickness), a refractive index of a tissues in the ophthalmic target (e.g., the cornea, aqueous humor, lens, or vitreous humor), or another measurement associated with a physical characteristic of the ophthalmic target. For example, views of the ophthalmic target associated with different beam paths can be aligned such that the respective surfaces of the ophthalmic target match for each view, as described above. In some cases, aligning the views may include generating a model with a parameterization of each of the tissues in the ophthalmic target, where the parameters include a refractive index for one or more of the tissues. A refractive index can then be determined by a best fit approach. For instance, a least squares technique can be used to align the parameterized models and determine a refractive index for one or more of the tissues of the ophthalmic target.

At 408, illumination light is emitted toward the ophthalmic target. The illumination light may be emitted by multiple illumination point sources that are arranged in a circular manner around the beam paths. For example, referring to FIG. 1A, the illumination point sources 116 may emit illumination light toward the ophthalmic target 120.

At 410, illumination light reflected by the ophthalmic target is received. The reflected illumination light may be received at one or more cameras device within the ophthalmic diagnostic system. The illumination light may include the illumination light transmitted at 408 by the illumination source and reflected back by the ophthalmic target. The reflected illumination light may travel along the beam path through which the OCT imaging beams. For example, referring to FIG. 1A, illumination light emitted by the illumination point sources 116 may be reflected by the ophthalmic target 120 and travel back along the beam paths 112 toward the beam splitter 108, which reflects a portion of the reflected illumination light toward the camera 106.

At 412, one or more curvatures of the ophthalmic target are determined based on the reflected illumination light. The curvatures may include an anterior corneal curvature, a posterior corneal curvature, or both. In some embodiments, by detecting first order Purkinje reflections of the illumination light on the front side of the cornea, the anterior corneal curvature can be determined. In some embodiments, by detecting second order Purkinje reflections on the backside of the cornea, the curvature of the posterior cornea can be determined. In some cases, a central curvature of the cornea (which may be undetectable using single-view OCT techniques) may be determined as well by, for example, parameterizing a corneal surface based on the off-axis perspective views of the ophthalmic target where reflections appear in the center area of the cornea (see, e.g., spots in the central area of views 152 and 156 of FIG. 1C).

At 414, a parameterized model of the ophthalmic target is selected or generated. The parameterized model may include a number of parameters that are associated with characteristics of the ophthalmic target. For example, the model may include parameters for all refractive surfaces and refractive indices of the various optical media (e.g., the cornea, aqueous humor, lens, vitreous humor, or other media) within the ophthalmic target. The model of the ophthalmic target may provide one or more simulated measurements or curvatures based on the parameters. For instance, the model may provide simulated measurements of refractive indices or curvatures of surfaces of the ophthalmic target.

At 416, the parameters of the model generated at 414 are optimized using characterizations and data collected in steps 406 and 412. The parameters may be optimized based on the measurements determined at 406, the curvatures determined at 412, or both. In some embodiments, the parameters may be optimized by minimizing differences between the observed measurements or curvatures (from 406, 412), and the simulated measurements or curvatures (from the model generated at 414). The minimization may be performed using a least squares method, or another minimization technique.

At 418 an IOL profile is determined based on optimized parameters determined at 416. The IOL profile may include one or more characteristics of an IOL to be inserted into the ophthalmic target. For example, the determined characteristics may be used to select or create an IOL replacement used in cataract surgery to replace an eye's natural lens. The IOL profile may include a power or shape of the IOL that most closely approximate that of the natural eye lens, or may include a relative position of the IOL within the ophthalmic target. The IOL profile may also include a media or an astigmatism of the IOL within the ophthalmic target, or other IOL characteristics. The IOL profile may be determined based on the measurements determined at 406, the curvatures determined at 412, or a combination thereof.

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer-readable storage medium for execution by, or to control the operation of, data-processing apparatus. A computer-readable storage medium can be, or can be included in, a computer-readable storage device, a computer-readable storage substrate, a random or serial access memory array or device, or a combination of one or more of them. Moreover, while a computer-readable storage medium is not a propagated signal, a computer-readable storage medium can be a source or destination of computer program instructions encoded in an artificially generated propagated signal. The computer-readable storage medium can also be, or be included in, one or more separate physical components or media (e.g., multiple CDs, disks, or other storage devices).

Some of the operations described in this specification can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). The computer system may include one or more data processing apparatuses coupled to computer-readable media storing one or more computer programs that may be executed by the one or more data processing apparatuses, and one or more interfaces for communicating with other computer systems.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Embodiments of the present disclosure provide systems and methods for obtaining diagnostic information about an ophthalmic target that may overcome limitations of conventional systems and methods. It will be appreciated that above-disclosed and other features and functions, or alternatives thereof, may be desirably combined into many other different systems or applications in accordance with the disclosure. It will also be appreciated that various presently unforeseen or unanticipated alternatives, modifications, variations, or improvements therein may be subsequently made by those skilled in the art which alternatives, variations and improvements are also intended to be encompassed by the following claims.

What is claimed is:

1. A multi-view diagnostic system, comprising:
an OCT engine;
a plurality of optical elements defining a plurality of beam paths between the OCT engine and an ophthalmic target, each beam path corresponding to a different viewing angle of the ophthalmic target;
a scanner configured to direct OCT imaging beams generated by the OCT engine toward the ophthalmic target along each respective beam path, direct first OCT imaging beams toward the ophthalmic target along a first beam path, wherein the first beam path corresponds to one of an optical axis and a visual axis of the ophthalmic target, and direct second OCT imaging beams toward the ophthalmic target along a second beam path defined by a set of static mirrors, wherein the second beam path intersects the first beam path within the ophthalmic target at an acute angle;
an illumination source configured to emit the illumination light, the illumination source comprising a plurality of illumination point sources arranged in one or more concentric patterns around an aperture that allows the OCT imaging beams or other light to pass through to or from the OCT engine;
a beam splitter optically aligned with the OCT engine and a camera optically aligned with the beam splitter, the camera configured to receive illumination light reflected by the ophthalmic target along each respective beam path; and
a processor and instructions stored in a memory, the instructions executable by the processor to:
determine a characteristic of the ophthalmic target based on OCT light reflected by the ophthalmic target along each respective beam path and detected by the OCT engine;
determine an optical intraocular lens (IOL) profile based on the ray tracing analysis and the detected OCT light, wherein the IOL profile includes a power, a shape, or a position of the IOL within the ophthalmic target; and
determine a characteristic of a cornea of the ophthalmic target based on the illumination light reflected by the ophthalmic target along each respective beam path.

2. The system of claim 1, wherein the instructions are further executable to determine a refractive index of at least one of a cornea, aqueous humor, a lens, or vitreous humor of the ophthalmic target based on the detected OCT light reflected by the ophthalmic target along each respective beam path.

3. The system of claim 1, wherein the instructions are further executable to generate a three-dimensional model of the ophthalmic target based on the detected OCT light.

4. The system of claim 1, wherein the plurality of beam paths comprises at least two beam paths which converge and intersect within the ophthalmic target.

5. The system of claim 1, wherein the instructions are further executable to perform a ray tracing analysis, the ray tracing analysis including a first or second order Purkinje ray tracing analysis.

6. The system of claim 1, wherein the scanner comprises one or more manipulatable mirrors that selectively direct the OCT imaging beams along one of the beam paths.

7. The system of claim 1, wherein the determined characteristic of the cornea includes an anterior corneal curvature or a posterior corneal curvature.

8. A method, comprising:
  directing multiple OCT imaging beams, from an OCT engine, toward an ophthalmic target along respective beam paths, each beam path defined by a plurality of optical elements and corresponding to a different viewing angle of the ophthalmic target, wherein directing the OCT imaging beams along multiple beam paths comprises:
    directing first OCT imaging beams toward the ophthalmic target along a first beam path, wherein the first beam path corresponds to one of an optical axis and a visual axis of the ophthalmic target; and
    directing second OCT imaging beams toward the ophthalmic target along a second beam path defined by a set of static mirrors, wherein the second beam path intersects the first beam path within the ophthalmic target at an acute angle,
  receiving, along each of the beam paths, reflected OCT light from the ophthalmic target;
  emitting, by a plurality of illumination point sources, illumination light toward an ophthalmic target, the illumination source comprising a plurality of illumination point sources arranged in one or more concentric patterns around an aperture that allows the OCT imaging beams or other light to pass through to or from the OCT engine;
  receiving illumination light reflected from the ophthalmic target along each of the beam paths;
  performing a ray tracing analysis based on the reflected illumination light; and
  receiving, via a beam splitter optically aligned with the OCT engine and a camera optically aligned with the beam splitter, illumination light reflected by the ophthalmic target along each respective beam path;
  determining one or more characteristics of the ophthalmic target based on the detected OCT light reflected by the ophthalmic target along each respective beam path; and
  determining an optical intraocular lens (IOL) profile based on the ray tracing analysis and the detected OCT light, wherein the IOL profile includes a power, a shape, or a position of the IOL within the ophthalmic target; and
  determining a characteristic of a cornea of the ophthalmic target based on the illumination light reflected by the ophthalmic target along each respective beam path and based on the ray tracing analysis.

9. The method of claim 8, wherein the determined characteristic of the ophthalmic target includes an anterior corneal curvature or a posterior corneal curvature.

10. The method of claim 8, wherein performing the ray tracing analysis comprises performing a first or second order Purkinje ray tracing analysis.

11. The method of claim 8, comprising generating a three-dimensional eye model of the ophthalmic target based on the detected OCT light reflected by the ophthalmic target along each respective beam path.

* * * * *